United States Patent [19]
Roychowdhury

[11] Patent Number: 6,090,266
[45] Date of Patent: *Jul. 18, 2000

[54] PROCESS FOR PRODUCTION OF HYDROGEN FROM ANAEROBICALLY DECOMPOSED ORGANIC MATERIALS

[76] Inventor: Sukomal Roychowdhury, 65 Floral Parkway, Floral Park, N.Y. 11001

[ * ] Notice: This patent issued on a continued prosecution application filed under 37 CFR 1.53(d), and is subject to the twenty year patent term provisions of 35 U.S.C. 154(a)(2).

[21] Appl. No.: 08/659,644

[22] Filed: Jun. 6, 1996

[51] Int. Cl.$^7$ ..................................................... C25B 1/02
[52] U.S. Cl. ........................... 205/637; 205/688; 205/698
[58] Field of Search .................... 205/688, 698, 205/637

[56] References Cited

U.S. PATENT DOCUMENTS

| | | | |
|---|---|---|---|
| 4,124,481 | 11/1978 | Ramer | 205/756 |
| 4,200,505 | 4/1980 | Day et al. | 205/639 |
| 4,341,608 | 7/1982 | St. John | 205/639 |
| 4,389,288 | 6/1983 | Vaughan | 205/637 |
| 4,395,316 | 7/1983 | St. John | 205/638 |

*Primary Examiner*—Arun S. Phasge
*Attorney, Agent, or Firm*—Whitman Breed; Abbott & Morgan LLP

[57] ABSTRACT

A process for the production of hydrogen from anaerobically decomposed organic materials by applying an electric potential to the anaerobically decomposed organic materials, including landfill materials and sewage, to form hydrogen, and for decreasing the time required to treat these anaerobically decomposed organic materials. The organic materials decompose to volatile acids such as acetic acid, which may be hydrolyzed by electric current to form hydrogen. The process may be continuously run in sewage digestion tanks with the continuous feed of sewage, at landfill sites, or at any site having a supply of anaerobically decomposed or decomposable organic materials.

10 Claims, 6 Drawing Sheets

PROCESS FOR PRODUCTION OF HYDROGEN FROM ANAEROBICALLY DECOMPOSED ORGANIC MATERIALS

BACKGROUND OF THE INVENTION

It is recognized that additional sources of energy are needed for America's sustained industrial growth. There exists an ever present danger in depending too heavily on fossil fuels, particularly those fuels imported from foreign sources. Fossil fuels (hydrocarbons) represent a limited supply of stored energy which may be released only during a combustion process. By burning hydrocarbons mankind has spewed billions of tons of toxic pollutants into the atmosphere. It therefore makes sense from both an environmental and economic standpoint to develop alternative sources of fuel.

Hydrogen is a fuel which does not produce pollutants, water being its only combustion product. Hydrogen has many industrial uses in the production of fertilizers, dyes, drugs, plastics, hydrogenated oils and fats and methanol and is used in many industries. It is also used as a rocket fuel.

1. Field of the Invention

This invention relates to a process for the production of hydrogen from anaerobically decomposed organic materials, including materials such as those found in landfill materials and sewage sludge, by applying an electric potential to and thereby creating a current through the anaerobically decomposed organic material and thereby forming hydrogen.

2. Description of Related Art

The established processes for producing hydrogen are: (1) steam reforming of hydrocarbons, (2) partial oxidation of coal, (3) electrolysis of water, and (4) direct use of solar radiation (photovoltaic method).

Steam-reformation of hydrocarbons and partial oxidation of coal are disadvantageous in that hydrocarbon fuels are consumed. Production of hydrogen by electrolysis of water, a relatively simple and non-polluting process, is costly and therefore economically disadvantageous for most industrial applications because the amount of energy needed for electrolysis of water exceeds the energy obtained from the combustion of the resulting hydrogen. Photovoltaic methods of hydrogen production have inherent inefficiencies related to access to solar radiation.

Unlike the methods for production of hydrogen outlined above, the process of the present invention does not depend on fossil fuels or the somewhat random appearance of sunlight to produce hydrogen. The present process converts what are typically waste materials into hydrogen, while simultaneously reducing the mass of said materials and/or reducing the treatment time of such materials by application of a relatively small electric potential to said materials. The process of this invention uses raw materials typically found in, among other places, municipal waste sites and sewage treatment plants and produces more energy, in the form of the chemically stored potential energy of hydrogen, than is required to produce the hydrogen.

A method of producing hydrogen from sugars is discussed in *Energy and the Environment*, Proceedings of the 1st World Renewable Energy Congress, Reading, UK, 23–28 September 1990. S. Roychowdhury and D. Cox ("Roychowdhury"). This method involves the production of hydrogen from pure sugars such as glucose or maltose.

Roychowdhury reports the initial production of hydrogen upon inoculation of a sugar solution with so-called "landfill inocula". To obtain landfill inocula, materials were obtained from various depths in a landfill, dried, ground (to obtain "landfill powder") and then incubated in situ. The incubated culture medium was observed to produce carbon dioxide and methane, primarily, and little else, indicating the presence of highly methanogenic flora in the innoculum. The supernatant from this culture medium, or in some cases the landfill powder, were used as inocula.

Roychowdhury discloses that upon inoculation of various sugar solutions with the landfill supernatant or landfill powder, the sugar solution produced hydrogen and carbon dioxide, and no methane or oxygen; indicating the presence of hydrogen-producing bacteria present in the landfill inoculum and/or landfill hydrogen. Hydrogen production decreased with increasing acidity, but could be increased by neutralizing the pH. A low voltage (approximately 3–4.5 V) electric current passed through Roychowdhury's sugar solution resulted in continuous hydrogen production, without neutralization. Variations of this technique were attempted with several combinations of inocula and sugar solutions, each resulting in sustained hydrogen production.

OBJECTS OF THE INVENTION

It is an object of this invention to provide a method for producing hydrogen from anaerobically decomposed organic materials.

It is another object of this invention to provide a method for producing hydrogen from anaerobically composted cellulosic materials.

It is another object of this invention to provide a method of producing hydrogen from anaerobically digested sewage sludge.

It is another object of this invention to provide a method for producing hydrogen from sewage sludge and from cellulosic landfill materials.

It is a further and related object of this invention to provide a method of reducing the weight and volume of cellulosic waste materials.

It is still a further object of this invention to provide a method for decreasing the time required to treat sewage sludge.

It is another object of this invention to provide a method of hydrogen production which does not require the use of fossil fuels.

SUMMARY OF THE INVENTION

This invention relates generally to a process which produces hydrogen from anaerobically decomposed organic materials such as anaerobicially composted cellulosic materials and anaerobically digested sewage sludge, and decreases the time required to treat anaerobically composted cellulosic materials and anaerobicaly digested sewage sludge. More specifically, the invention relates to a method wherein a relatively low electric potential is applied to anaerobically decomposed organic materials such as anaerobically composted cellulosic waste materials and anaerobically digested sewage sludge which, as a result of anaerobic decomposition, have been fermented into "volatile" carboxylic acids such as acetic acid. The electric current resulting from the application of an electric potential is believed to hydrolyze the acetic acids and other volatile carboxylic acids within the decomposed materials, thereby producing hydrogen. Formation of methane is suppressed. Organic mass, such as solids contained within sewage sludge is reduced at an increased rate, and the time required to treat waste materials such as sewage sludge is thereby reduced.

DETAILED DESCRIPTION OF THE INVENTION

The process of the present invention may typically be practiced at any large municipal landfill or sewage treatment facility, but can be practiced on a smaller scale wherever anaerobically decomposed organics such as anaerobically composted cellulosic materials or anaerobically digested sewages sludge are found or may be generated.

Anaerobically composted cellulosic materials are typically found in landfill materials. Anaerobically digested sewage sludge typically comprises sludge found at munipical sewage treatment plants. Landfill materials generally consist of approximately 70% cellulosic materials and have a moisture content of 36% to 46%. Sewage sludge is primarily liquid, contains volatile acids such as acetic acid, and includes 2–3% solids. Both landfill materials and sewage sludge naturally contain methane-producing bacterial species and hydrogen-producing bacterial species.

The invention is practiced by applying an electric potential of between 1.5 and 6.5 volts, preferably between 3 and 6 volts, most preferably between 3.0 and 4.5 volts to, and thereby passing a electric current through, anaerobically decomposed organic materials such as landfill materials or sewage sludge. This electric potential is applied through electrodes which are preferably made from lead, copper, steel or brass, more preferably from cast iron bars, and most preferably from copper impregnated graphite.

Anaerobic decomposition, specifically anaerobic composting and anaerobic digestion, refers to a process where organic compounds, typically but not limited to compounds of the general formula $C_nH_{2n}O_n$, decompose in the absence of an oxygen environment. Volatile acids such as acetic acid are typically formed by such anaerobic decomposition. Although anaerobic decomposition may in some instances be preceded by aerobic decomposition, aerobic decomposition is not a prerequisite to anaerobic decomposition and electrodes can be placed within the organic materials prior to the commencement of anaerobic decomposition.

As described above, both landfill materials comprising anaerobically composted cellulosic materials and anaerobically digested sewage sludge contain relatively high amounts of volatile acids such as acetic acid. These acids are known to act as electrolytes. In practicing the invention, one or more sets of electrodes may be placed within landfill material or sewage sludge in such a way that an electric potential is applied, resulting in an electrical current. Electrode distance and placement may be adjusted to achieve these conditions. The voltage, average placement of electrodes and number of electrodes will vary depending upon the size and composition of the landfill material or sewage sludge sought to be used to produce hydrogen. Electrode sets, may be of any suitable shape, e.g. plates, bars, grids, etc.

In a preferred embodiment of the invention, each individual electrode is placed into landfill materials and is surrounded by an inert "cage" which effectively ensures that the moisture component of the landfill materials, and not a component which might interfere with electrical activity, is immediately adjacent each electrode. Placement of the electrodes in a suitable position within the landfill material may require some trial and error.

When an electric potential is applied, hydrogen production begins and production of hydrogen increases to from 70% to 75% by volume of the total gases produced. The level of methane produced decreases from a high of approximately 70% by volume of the total gases produced, when the electric current is first applied, to trace levels. Carbon dioxide and nitrogen production remain relatively constant and do not vary significantly with methane or hydrogen production.

Without being bound by theory, it is believed that the essence of the electrochemistry of this invention is the electrolysis of low molecular weight volatile acids such as acetic acid produced by bacterial breakdown of carbohydrates and other nutrients. Because oxygen production is not observed, it is believed that electrolysis of water is not a source of hydrogen. It is further believed that hydrogen gas produced by the electrolysis of volatiles present in the sludge and in landfill materials, inhibits the activity of methanogenic species.

In a preferred embodiment, cellulosic materials and/or sewage sludge are made to decompose "on-site", i.e., in a localized bin or chamber, rather than at a centralized landfill or sewage treatment facility. The anaerobically composted cellulosic waste materials and/or the anaerobically digested sewage sludge are then optionally taken to a transfer station equipped with electrodes as previously described to produce hydrogen, or alternatively made to produce hydrogen "on-site" by application of electric potential at or near the on-site bin or chamber. In this alternate embodiment, hydrogen could then be stored or used on-sites as a energy source.

EXAMPLES

Electrodes:

Electrodes were cast iron bars, 300 mm long, 25 mm wide and 2.5 mm thick. Other metallic electrodes were used such as lead, copper, steel, brass and others. A pair of copper impregnated graphite electrodes of the same size was used. Degradation of the electrode was not very noticeable.

Landfill Materials:

Samples of landfill material were obtained from a sanitary landfill at Staten Island New York from a depth of between 30 and 50 feet. The landfill materials naturally produce methane and carbon dioxide as primary gases (55:35) through methanogenesis.

Sludge:

Sludge samples were taken from a primary digester of a sewage treatment plant at Brooklyn, N.Y. Sewage sludge produces methane and carbon dioxide (65:30) by methanogenesis.

Special Apparatus:

A series of experiments were set up to determine whether the production of hydrogen would take place when current was passed through either sewage sludge or through landfill materials. The pH of the sludge was 7.0–7.5 and the pH of the landfill material was 6.5–7.0. Apparatus included an 800 ml flask with a three hole rubber stopper. Two of those holes were fitted with electrodes and the third hole had a glass delivery tube. The electrodes were connected across two 1.5 volt batteries in series, resulting in a potential of 3.0 volts. The apparatus was placed in an incubator set either at 37° C. or at 55° C. Other apparatus included a New Brunswick Fermenter using a 6–8 liter glass vessel where the temperature, and rotating stirrer and a cooling system could be controlled at a desired setting.

EXPERIMENTAL DATA:

Example 1

Figure 1:
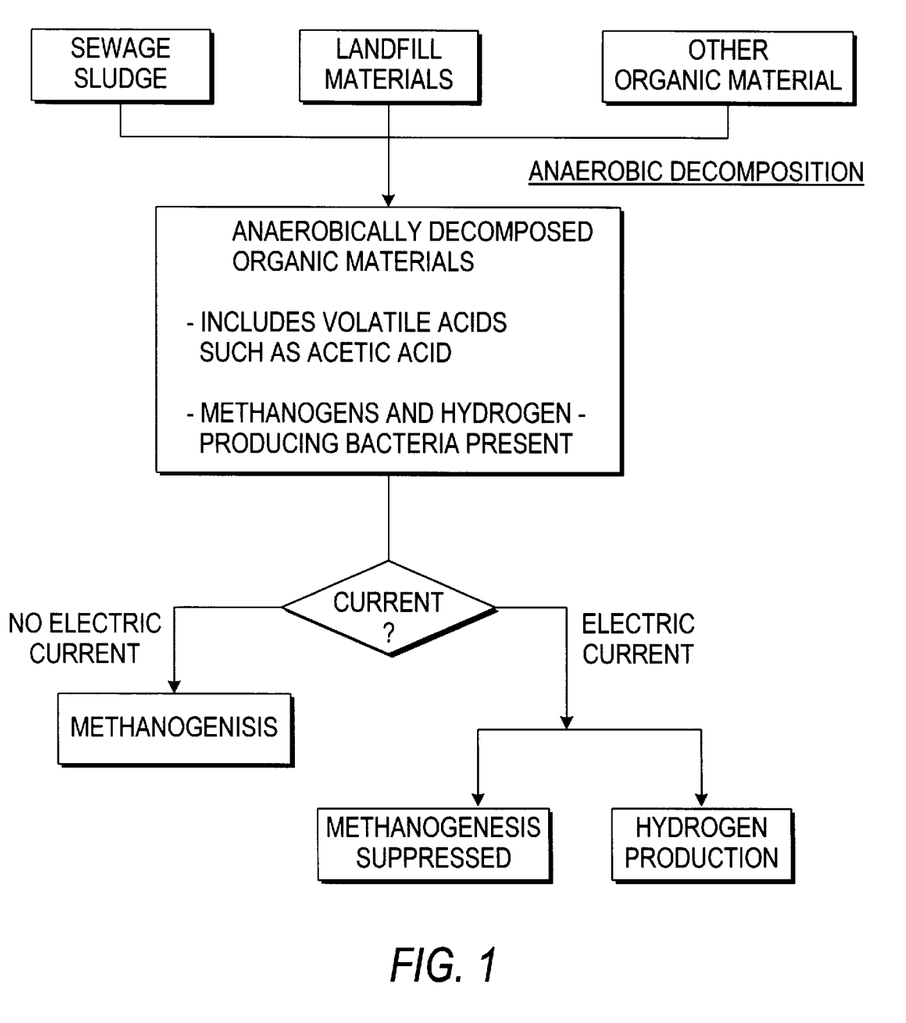
FIG. 1 is a flow chart showing both production of hydrogen and suppression of methanogenesis from anaerobically decomposed organic materials in the presence of an electric current, and methanogenesis from anaerobically decomposed organic materials in the absence of an electric current.
Figure 2:
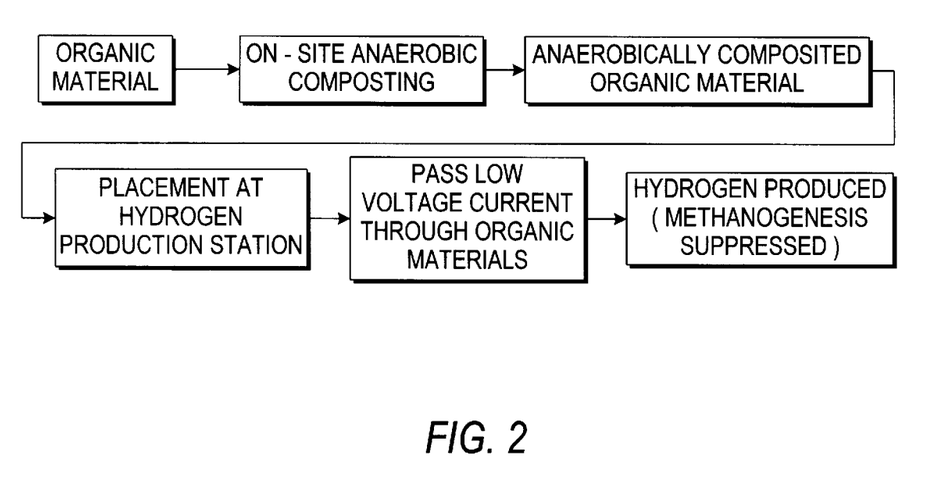
FIG. 2 is a flow chart showing a process for production of hydrogen which includes on-site anaerobic decomposition of organic materials.
Figure 3:
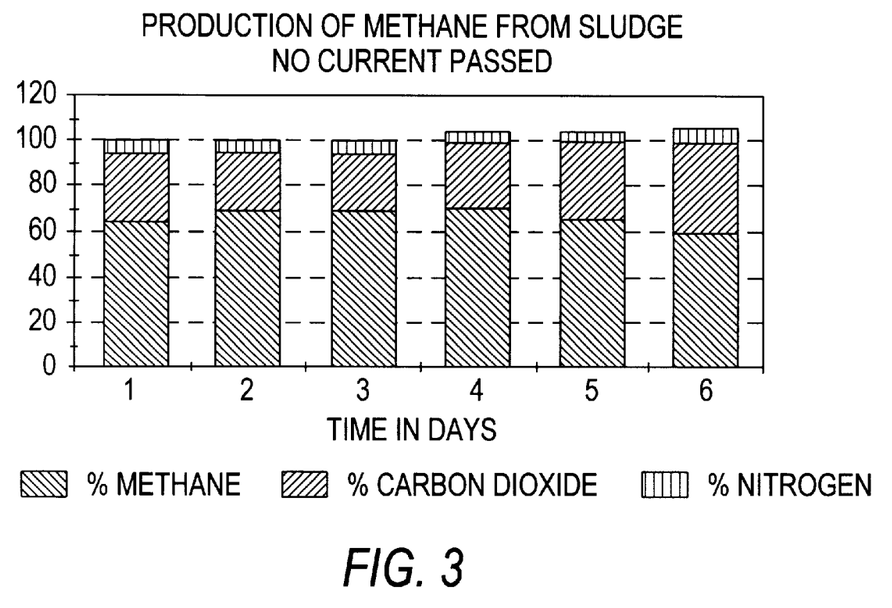
FIG. 3 is a bar graph representation of the information in Table 1.

As an experimental control, freshly obtained sewage sludge in an 800 ml flask was placed at 37° C. in an incubator gases, including primarily methane, were produced as described at Table 1 and depicted at FIG. 3.

TABLE 1

Production of $CH_4$ and $CO_2$

| DAYS | % $CH_4$ | % $CO_2$ | % $N_2$ |
|---|---|---|---|
| 1 | 65 | 30 | 5 |
| 2 | 70 | 25 | 5 |
| 3 | 70 | 25 | 5 |
| 4 | 65 | 30 | 4 |
| 5 | 60 | 35 | 4 |
| 6 | 55 | 40 | 5 |

Example 2 sewage sludge from the primary digester was placed in an 800 ml flask which was then placed in a preheated incubator at 37° C. Methane gas was generated. As soon as optimum production of methane was achieved, a current was passed through the liquid in the flask. The production of methane gas declined gradually and hydrogen and carbon dioxide were produced. Methane was completely suppressed when production of hydrogen reached its peak, as described at Table 2 and depicted at FIG. 4.

TABLE 2

Figure 4:
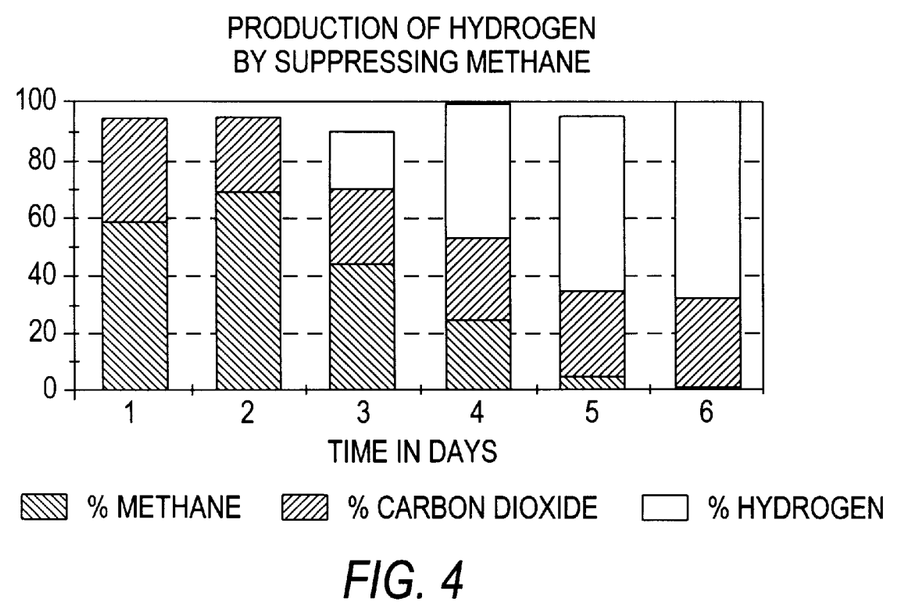
FIG. 4 is a bar graph representation of the information in Table 3.

Production of $H_2$ and suppression of $CH_4$

| DAYS | % $CH_4$ | % $CO_2$ | % $H_2$ |
|---|---|---|---|
| 1 | 60 | 35 | — |
| 2 | 70 | 25 | — |
| As and when current was passed | | | |
| 3 | 45 | 25 | 20 |
| 4 | 25 | 28 | 46 |
| 5 | 5 | 30 | 60 |
| 6 | TR | 30 | 68 |

Example 3

Sewage sludge from the primary digester was placed in an 800 ml flask which was then placed in an incubator at 37° C. A current was passed through the sludge, applying 3 volts, using the two 1.5 volt batteries in series. Very little methane was produced at the beginning. Within 3 days, production of hydrogen reached its peak and methane gas was totally suppressed, as described at Table 3 and depicted at FIG. 5.

TABLE 3

Figure 5:
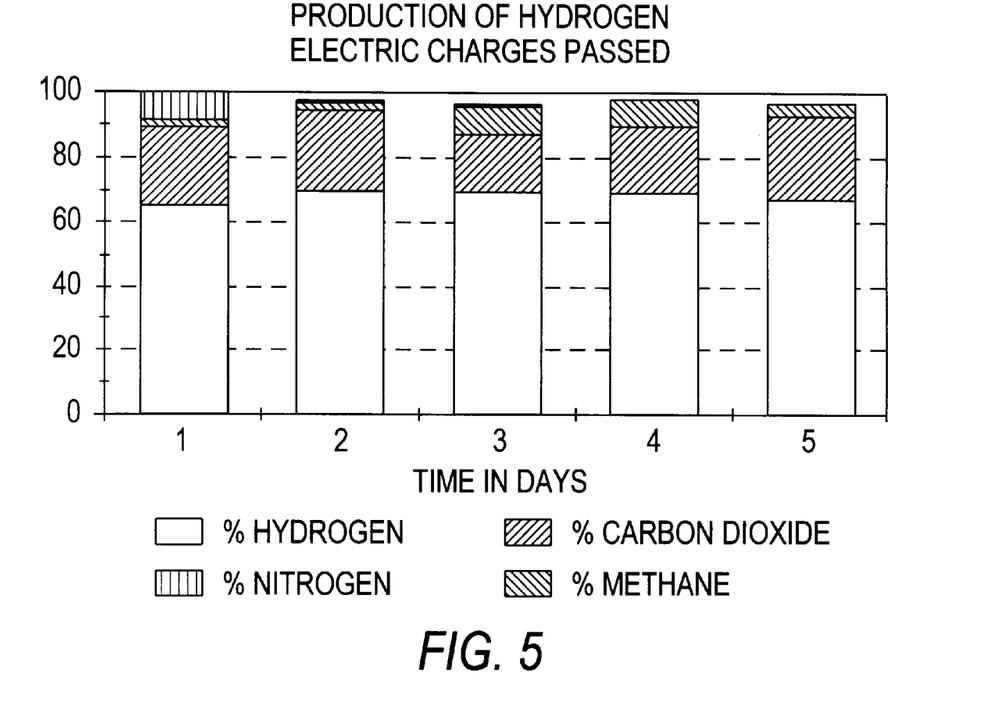
FIG. 5 is a bar graph representation of the information in Table 3.

Production of $H_2$ and $CO_2$ When Electric Charges Were Passed From the Start

| DAYS | % $H_2$ | % $CO_2$ | % $N_2$ | % $CH_4$ |
|---|---|---|---|---|
| 1 | 65 | 25 | 2 | 8 |
| 2 | 70 | 25 | 2 | TR |
| 3 | 70 | 18 | 8 | TR |
| 4 | 70 | 20 | 8 | — |
| 5 | 68 | 25 | 4 | — |

Example 4

Sewage sludge sample was placed in a five liter flask in the New Brunswick Fermenter and 4 electrodes were introduced. Electrical current was passed through (2.5 volts and 0.05 to 0.07 Amps). In the beginning only methane and carbon dioxide were produced with the very little hydrogen. As soon as the voltage was increased to 4.0–4.5, and current to 0.11–0.15 Amps, methane was gradually suppressed and hydrogen was produced as described at Table 4.

TABLE 4

Production of $H_2$ and $CO_2$ From Sludge in 5 Liter Container

| DAYS | % $H_2$ | % $CO_2$ | % $N_2$ | % $CH_4$ |
|---|---|---|---|---|
| 1 | — | 30 | 12 | 50 |
| 2 | 5 | 35 | 8 | 46 |
| 3 | 4 | 30 | 6 | 60 |
| Voltage Was Increased to 4–4.5 Volts, A = .1 to .17 | | | | |
| 5 | 25 | 30 | 5 | 40 |
| 6 | 48 | 25 | 5 | 20 |
| 7 | 60 | 20 | 2 | 8 |
| 9 | 70 | 25 | 4 | TR |

Example 5

Similar experiments were set up with landfill materials (composted municipal solid wastes) in two 800 ml flasks, (1) with landfill materials only, (2) with landfill materials where electrode were dipped in. The results are described at Tables 5 and 6, and depicted at FIGS. 6 and 7.

TABLE 5

Production of Gases From Landfill Materials

Figure 6:
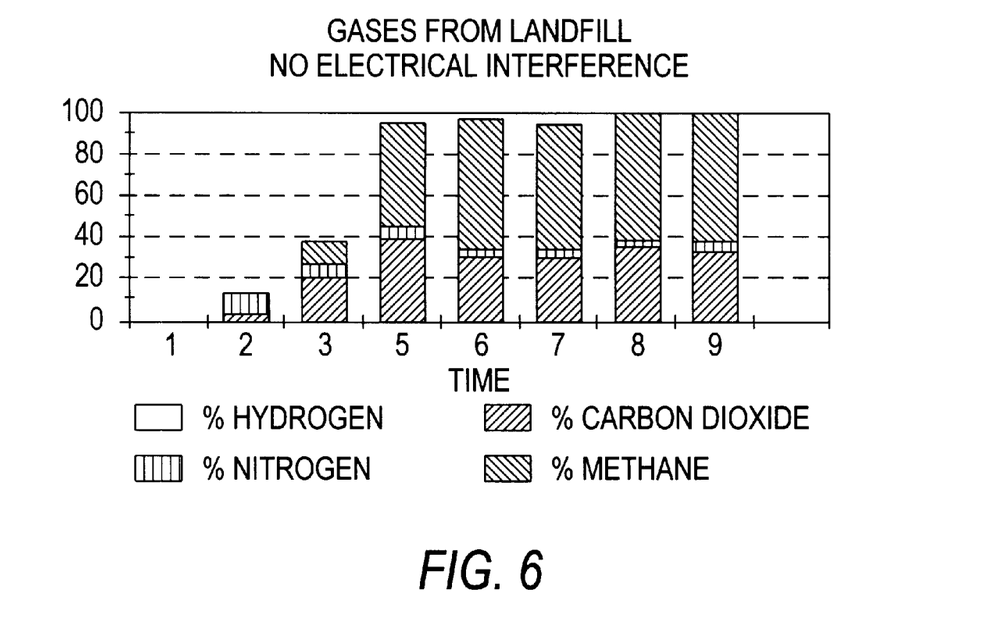
FIG. 6 is a bar graph representation of the information in Table 5.

| DAYS | % $H_2$ | % $CO_2$ | % $N_2$ | % $CH_4$ |
|---|---|---|---|---|
| 1 | — | — | — | — |
| 2 | — | 3 | 10 | — |
| 3 | — | 20 | 8 | 10 |
| 5 | — | 40 | 6 | 50 |
| 6 | — | 30 | 5 | 63 |
| 7 | — | 30 | 5 | 60 |
| 8 | — | 35 | 4 | 60 |
| 9 | — | 33 | 5 | 62 |

TABLE 6

Production of Gases From Landfill Materials in Presence Of Electrodes

Figure 7:
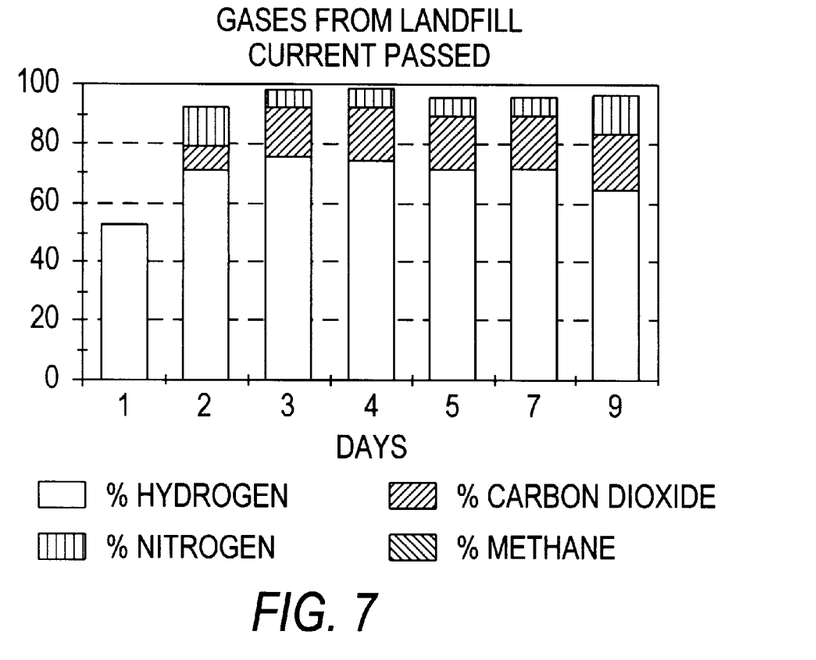
FIG. 7 is a bar graph representation of the information in Table 6.

| DAYS | % $H_2$ | % $CO_2$ | % $N_2$ | % $CH_4$ | TOTAL CC |
|---|---|---|---|---|---|
| 1 | 53 | — | All | — | 95 |
| 2 | 72 | 8 | 13 | — | 302 |
| 3 | 76 | 17 | 6 | — | 500 |
| 4 | 75 | 18 | 6 | — | 600 |
| 5 | 72 | 18 | 6 | — | 450 |
| 7 | 72 | 18 | 6 | — | 600 |
| 9 | 65 | 18 | 14 | — | 500 |

Example 6

Example 5 was repeated: (1) with sludge only, (2) with sludge having operating electrodes. The results are described at Table 7 and 8, and depicted at FIG. 8.

TABLE 7

Production of Gases From Sludge in Absence of Electrodes

| DAYS | % $H_2$ | % $CO_2$ | % $N_2$ | % $CH_4$ | TOTAL CC |
|---|---|---|---|---|---|
| 2 | — | 20 | 14 | 65 | 50 |
| 3 | — | 14 | 10 | 70 | 125 |
| 4 | — | 19 | 4 | 72 | 225 |
| 5 | — | 22 | 4 | 66 | 258 |
| 6 | — | 18 | 8 | 70 | 200 |

TABLE 8

Production of Gases From Sludge in Presence of Electrodes

Figure 8:
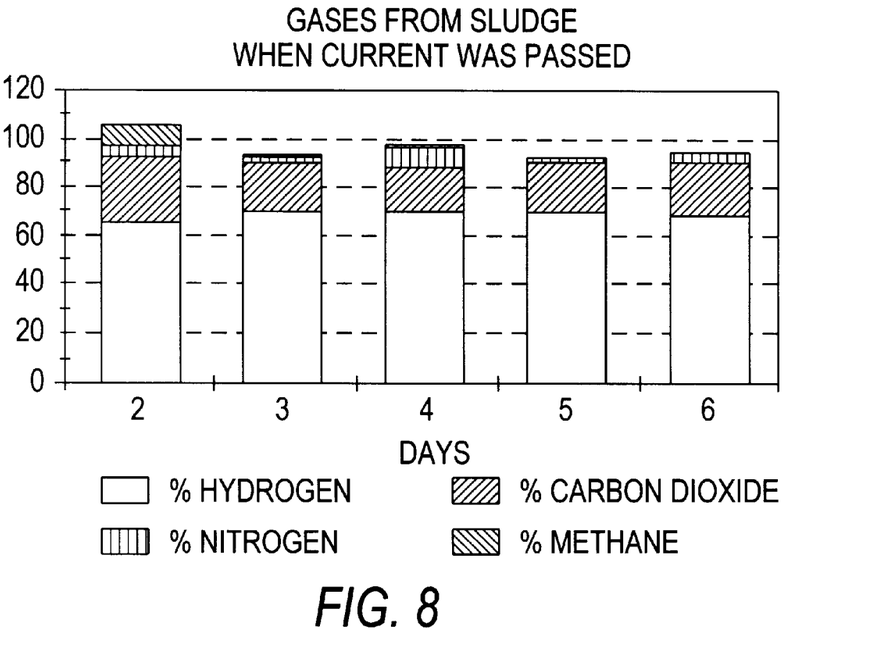
FIG. 8 is a bar graph representation of the information in Table 8.

| DAYS | % $H_2$ | % $CO_2$ | % $N_2$ | % $CH_4$ | TOTAL CC |
|---|---|---|---|---|---|
| 2 | 65 | 28 | 4 | 8 | 85 |
| 3 | 70 | 20 | 2 | TR | 200 |
| 4 | 70 | 18 | 8 | TR | 310 |
| 5 | 70 | 20 | 2 | — | 330 |
| 6 | 68 | 22 | 4 | — | 258 |

Example 7

An experiment was set up with landfill materials in a 6 liter vessel with electrodes. A current was created through the landfill materials by applying an electric potential of 3.5 V. The results are described at Table 9 and depicted at FIG. 9.

TABLE 9

Figure 9:
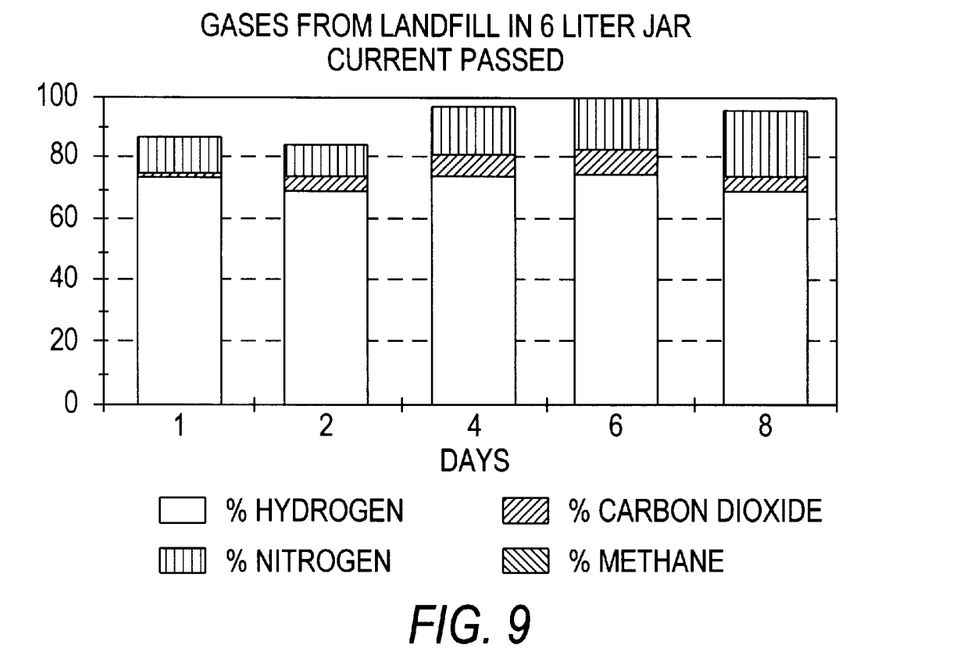
FIG. 9 is a bar graph representation of the information in Table 9.

Production of Gases From Landfill Materials in 6 Liter Vessel With Electrodes

| DAYS | % $H_2$ | % $CO_2$ | % $N_2$ | % $CH_4$ | TOTAL |
|---|---|---|---|---|---|
| 1 | 75 | TR | 12 | — | 100 |
| 2 | 70 | 5 | 10 | — | 1020 |
| 4 | 75 | 7 | 15 | — | 850 |
| 6 | 75 | 8 | 17 | — | 750 |
| 8 | 70 | 5 | 20 | — | 600 |

Example 8

Landfill materials in a 6 liter vessel were placed in a preheated incubator at 55° C. After 4 days electrodes were connected to 3.5 volt terminals. The results are described at Table 10, and depicted at FIG. 10.

TABLE 10

Figure 10:
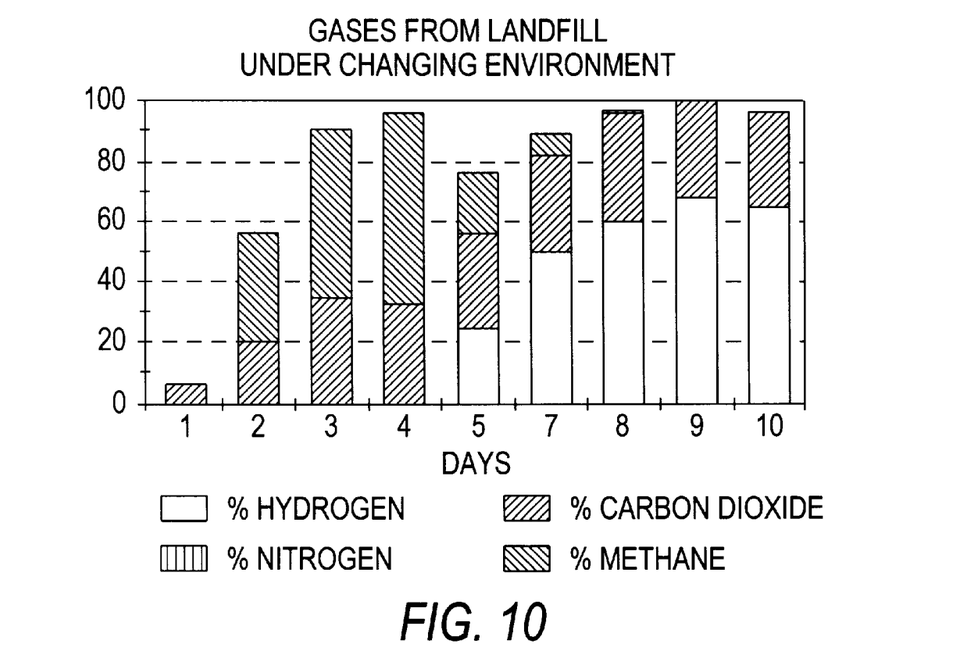
FIG. 10 is a bar graph representation of the information in Table 10.

Production of Gas From Landfill Materials in Two Different Environment In the Same Set Up

| DAYS | % $H_2$ | % $CO_2$ | % $N_2$ | % $CH_4$ | TOTAL |
|---|---|---|---|---|---|
| 1 | — | 5 | All | — | 20 |
| 2 | — | 20 | | 35 | 125 |
| 3 | — | 35 | | 55 | 200 |
| 4 | — | 32 | | 63 | 200 |
| At this stage electric charges were passed, V = 3.5, | | | | | |
| 5 | 25 | 30 | | 20 | 150 |
| 7 | 50 | 31 | | 7 | 200 |
| 8 | 60 | 35 | | TR | 250 |
| 9 | 68 | 31 | | — | 285 |
| 10 | 65 | 30 | | — | 200 |

What is claimed is:

1. A process for producing a gas stream from anaerobically digested organic materials containing volatile carboxylic acids formed during the anaerobic digestion of said organic materials, by the action of bacteria contained therein, said gas stream having enhanced levels of hydrogen and suppressed levels of methane relative to gases inherently produced from said anaerobically digested organic materials, comprising:

(a) forming a reaction mass comprising said anaerobically digested organic materials;

(b) maintaining said reaction mass under anaerobic conditions;

(c) applying an electric potential across said reaction mass to cause the production of said gas stream containing enhanced amounts of hydrogen and suppressed amounts of methane; and, (d) collecting said gas stream.

2. A process as recited in claim 1, wherein said reaction mass consists essentially of said anaerobically digested organic materials.

3. A process as recited in claim 2, wherein said anaerobic digestion of said organic materials takes place by the action of indigenous anaerobic bacteria contained therein.

4. A process as recited in claim 1, wherein said reaction mass is formed without addition of extrinsic electrolyte.

5. A process as recited in claim 1, wherein said reaction mass is formed without addition of extrinsic water.

6. A process as recited in claim 1, wherein said electrical potential is from about 1.5 to about 6.5 volts.

7. A process as recited in claim 6, wherein said electrical potential is from about 3.0 to about 4.5 volts.

8. A process as recited in claim 1, wherein said reaction mass is comprised of sewage sludge.

9. A process as recited in claim 1, wherein multiple pairs of electrodes are employed for applying electrical potential.

10. A process for producing an economically valuable gas stream from anaerobically digested organic materials containing volatile carboxylic acids formed during the anaerobic digestion of said organic materials by the action of bacteria contained therein, said gas stream having enhanced levels of hydrogen and suppressed levels of methane relative to gases inherently produced from said anaerobically digested organic materials, comprising:

(a) forming a reaction mass comprising said anaerobically digested organic materials;

(b) maintaining said reaction mass under anaerobic conditions;

(c) applying an electric potential across said reaction mass to cause the electrolysis of said carboxylic acids but not the electrolysis of water contained in said reaction mass, thereby causing the production of said gas stream containing enhanced amounts of hydrogen and suppressed amounts of methane; and, (d) collecting a gas stream from said reaction mass substantially free of oxygen.

* * * * *